United States Patent [19]

Suhonen

[11] Patent Number: 6,007,334
[45] Date of Patent: Dec. 28, 1999

[54] INTERDENTAL BALLOON

[75] Inventor: Jouko Suhonen, Kloten, Switzerland

[73] Assignee: Schneider (Europe) GmbH, Bulach, Switzerland

[21] Appl. No.: 08/985,884

[22] Filed: Dec. 5, 1997

[30] Foreign Application Priority Data

Feb. 25, 1997 [EP] European Pat. Off. .............. 97103023

[51] Int. Cl.⁶ .................................................... A61C 5/04
[52] U.S. Cl. .............................. 433/39; 433/149; 433/80; 604/49
[58] Field of Search ............................... 433/39, 149, 80, 433/136, 148, 229; 604/96

[56] References Cited

U.S. PATENT DOCUMENTS

| | | | |
|---|---|---|---|
| 2,311,158 | 2/1943 | Conway et al. | 32/17 |
| 3,473,226 | 10/1969 | Arlers et al. | 433/149 |
| 3,815,243 | 6/1974 | Eames | 32/63 |
| 3,890,714 | 6/1975 | Gores | 433/149 |
| 4,337,041 | 6/1982 | Harsany | 433/149 |
| 5,421,725 | 6/1995 | Weissenfluh | 433/149 |
| 5,527,181 | 6/1996 | Rawls et al. | 433/136 |
| 5,573,400 | 11/1996 | Asher | 433/136 |
| 5,738,653 | 4/1998 | Pinchuk et al. | 604/96 |
| 5,743,738 | 4/1998 | Baffelli et al. | 433/149 |
| 5,749,849 | 5/1998 | Engelson | 604/96 |
| 5,749,888 | 5/1998 | Yock | 604/96 |

FOREIGN PATENT DOCUMENTS

| 0668060 A2 | 8/1995 | European Pat. Off. . |
|---|---|---|
| 2323367 | 4/1977 | France . |

OTHER PUBLICATIONS

Search Report dated Jul. 30, 1997 in corresponding European Patent Application No. 97103023.4, together with Communication and one–page Annex.

*Primary Examiner*—Gene Mancene
*Assistant Examiner*—Pedro Philogene

[57] ABSTRACT

The dental device comprises an elongated inflatable balloon for placement around a matrix band in part surrounding relationship with a decayed tooth. Upon inflation, the balloon evenly applies the matrix band against the tooth.

11 Claims, 9 Drawing Sheets

INTERDENTAL BALLOON

BACKGROUND OF THE INVENTION

This application is based upon European Patent Application No. 97103023.4 filed in the European Patent Office on Feb. 25, 1997, the priority of which is hereby claimed under 35 U.S.C. § 119. This invention relates to a dental medicine device for pressing a wall molding means against a decayed tooth for restoration thereof, comprising expandable means for urging said wall molding means against the decayed tooth wall to hold restorative material inserted into the tooth.

Dental restoration of cavities between teeth is common practice in dentistry. When it is necessary to restore the portion of a tooth which, prior to decay, contacted an adjacent tooth, it is indispensable to confine the restoration material during placement and until rigid enough, to support itself to conform exactly to the healthy portion of the tooth. Any surplus or overhang of restorative material in the hardly reachable approximal areas constitutes an irritation source which leads to plaque accumulation and constitutes enormous niches for the cariogenic flora. With time, the initially gram-positive flora transforms into parodontopathogenic gram-negative flora which leads to acute and/or chronic periodontal disease.

In order to position the restorative material, it is customary to fit, by means of an appropriate tensioner also called retainer or holder, a matrix band around the tooth for creating a mold to replace the wall lost by caries and cavity preparation during insertion of the restorative material into the tooth. To achieve its function, the matrix band must be fixed in position, and it must be formed as close as possible to the shape of the tooth so that the restorative material placed therein will conform to the outer surface of the healthy portion of the tooth. However, because of the convexity or concavity of the tooth at the site of restoration, the matrix band tends to stand away from the tooth, thereby allowing surplus or overhang of the restoration material to pass between the tooth and the matrix band. This is especially the case when bonding agents and/or flowable composite materials are used to restore the tooth.

Accordingly, a wedging of the matrix band is made, by means of a wedge which is forced between the adjacent teeth in the region between the former contact point and the gingiva to press the matrix band material against the tooth at the floor of the cavity preparation. The wedge is also aiming to perform an additional function in that it forces the teeth apart creating a wider space therebetween than would normally exist. This is important because the matrix band occupies an amount of space which would persist when the matrix band is removed if the elastic memory of the periodontal membrane would not move the teeth closer together after removal of the wedge which caused the temporary separation.

Typical wedging technique provides for tapered elongated wooden wedges which may be inserted between adjacent teeth with friction being relied upon to maintain the wedge in position. Since the interdental papilla occupies the approximal space between the teeth, insertion of the wedge causes an injury inducing rubbing compression to the tissue between the teeth. Furthermore, the wedge tends to slip out of position due to the poor frictional engagement provided. As the material forming the wedge is only slightly deformable with practically no elastic memory, all the force applied for placement of the wedge is transmitted to the attachment of the teeth to the bone, with the risk of trauma at this level, whereby the force created by the wedge can be lost. And, most of all, as the tooth contour is quite variable at the site of restoration, with discontinuities and convexities, respectively concavities bordered with convexities, wedge cannot provide more than tangential or point contact between the wedge, the matrix band and the tooth. There is therefore significant pressure on the matrix band area where convexity of the tooth is most pronounced; other areas of the matrix band get only mild pressure or no pressure at all. The result is a loose fit of the matrix band to the tooth, with unavoidable surplus or overhangs of restorative material between the tooth and the matrix band. Of course, it is possible to try to tailor the wedge in an attempt to provide a better fit between wedge, matrix band and tooth; however, this is time consuming and the result is quite aleatory because of difficult to ascertain parameters such as the complex geometry of the tooth and the advance of the wedge between the teeth to assume the required friction fit and pressure of the wedge on the matrix band and tooth.

Where composite resin restorations for light curing technique are used, light transmitting plastic wedges have been developed to transfer light energy for curing of the restorative material. The problems outlined hereabove remain however unsolved, with the added risk that surplus and overhangs of the restorative material may result in leaks in the restorative material which may induce cracks or hollow spaces in the material, thereby reducing its efficiency and creating further niches for the pathogenic flora.

There has been various attempts to provide better wedging. For example, U.S. Pat. No. 3,890,714 shows a plastic wedge with a dihedral body the lateral walls of which are flexible and slotted to increase the friction coefficient between the wedge and adjacent elements; although possibly reducing the risk of trauma at attachment level of the teeth and raising the friction anchor between the teeth, this wedge still cannot solve the problem of a loose matrix band fit; in addition, this wedge has a tendency to lacerate the gingival tissue.

U.S. Pat. No. 3,815,243 discloses a trihedral wedge of soft plastic material with serrations defined by transverse protrusions intended to more evenly distribute the pressure; although outlining the problem of poor matrix band application resulting in surplus of restorative material between the tooth and the matrix band, this wedge still cannot solve that problem because the serrations cannot evenly match the discontinuities, convexities, and concavities of the tooth contour at the site of restoration.

U.S. Pat. No. 4,337,041 refers to a wedge the elongated body of which is provided with depressions intended to positively engage the teeth and simulate the contour of the concave interdental papilla. The wedge is thus preshaped and it can consequently not match the tooth shapes which are different in each case of restoration. The problem of uneven pressure for the matrix band is thus unsolved. In addition, the edges of the depression simulating the contact of the interdental papilla may lacerate the tissue upon insertion of the wedge.

U.S. Pat. No. 5,573,400 describes an expanding dental wedge having a trihedral elongated tapered body. Other cross-sectioned shapes such as trapezoidal or round are possible. This wedge is made of compressed hydrophilic material, such as cellulose or synthetic foams, that expand in contact with moisture. Accordingly, after placement of the matrix band, the wedge is inserted conventionally into the interproximal area between teeth. At this stage, addition of moisture is required to begin an expansion process. The moisture may be applied by the practitioner in the form of water and moisture from the interproximal tissues is said to also enter into matter for the expansion process. The document indicates that the moisture causes a pronounced expansion of the compressed material, providing reciprocal pressure to all points of the matrix band along the proximal surface, thus providing a matrix band seal. The document also indicates that the wedge is more gentle to interdental tissues due to its pliable nature when in contact with moisture. Although this technology may appear appealing, there are serious drawbacks. The expansion and pressure which may result therefrom are totally uncontrollable. The rate of expansion with respect to the amount of moisture is unknown; it is not only bound to the moisture applied by the practitioner, it also depends from variations of the moisture conditions of the gingival tissue and bucal environment, and it further varies as a function of the homogeneity of the compressed material along the length of the wedge. The practitioner has absolutely no means to know how the pressure resulting from the expansion will distribute. The pressure resulting from the expansion may be too low to properly apply the matrix band to sharp convexities or concavities or irregularities of the tooth contour, whereby the risk of poor or loose positioning of the matrix band against the tooth, and the added risk of insufficient force to take the teeth apart from one another. If the pressure is too high than would be required for proper application of the matrix band to the tooth contour there is the added risk of trauma for the teeth attachment. Once the moisture expansion initiated, there is no way to stop or to reduce it otherwise than by a difficult if not impossible drying procedure, whereby the practitioner cannot change the matrix band positioning if he deems it advisable to do so before the restorative material filling procedure. The system therefore cannot be failproof to avoid the risk of surplus or overhangs of restorative material between the tooth and matrix band and the risk of trauma. Apart of this, the document is silent as to how the expanded wedge may be withdrawn from the interdental papilla; forcible withdrawal of the expanded wedge may cause injury to the interdental papilla as well as it may cause an overspacing of the teeth from one another and consequent trauma. Furthermore, rubbing insertion of the compressed dried material may also cause injury to the interdental papilla. And the compressed expandable material forming the wedge does not appear to be appropriate for the transmission of light energy as required for curing plastic or composite restorative materials. Moreover, the wedge is contraproductive since successful handling of filling materials requires 100% dryness. Moisture reduces the quality of restorations. Thus a rubber dam is to be applied to keep the operated area dry.

All references cited herein, including the foregoing, are incorporated herein in their entireties for all purposes.

SUMMARY OF THE INVENTION

It is an object of the invention to provide a dental medicine device avoiding the aforesaid drawbacks. A further object of the invention is a dental medicine device which simplifies the matrix band installation in dental restoration procedures. Still a further object of the invention is a dental medicine device that is versatile and enhances the quality of restoration procedures.

Accordingly, where the expandable means comprise inflatable flexible container means for urging the wall molding means against the decayed tooth wall, an even pressure may be applied to the wall molding means upon mere inflation of the inflatable flexible container means, whatever the discontinuities, convexities or concavities of the tooth contour. There is no more risk of having the wall molding means poorly or loosely applied to the tooth contour, which eliminates the risk of surplus or overhangs of restorative material between the wall molding means and the tooth. As the inflatable flexible container means are deformable with high elastic memory, the distribution of force is not limited to the attachment of the teeth to the bone, the risk of trauma at this level is strongly reduced, and there is no risk of loosing the force created by the inflatable flexible container means which cannot slip out of the interdental space. Insertion of the inflatable flexible container means into the space between the teeth may be made with the inflatable flexible container means in deflated condition through the spacing created between the teeth by the restoration cavity preparation, with no risk of injury at interdental papilla level. The expansion of the inflatable flexible container means is fully controllable, merely depending on inflation which may be obtained by simple and reliable inflation fluid supplying means such as for example a syringe or a pump. Of course, inflation fluid may be a liquid or a gas, whatever the nature of its generation. The practitioner may at any time raise or reduce the pressure exerted by the inflatable flexible container means as well as he may easily interrupt the inflation procedure to modify the positioning of the wall molding means before the restorative material filling procedure. And withdrawal of the inflatable flexible container means is simplest, being sufficient to deflate them for having them out of the interdental space. And as the inflatable flexible container means precisely and efficiently position and hold the wall molding means where needed, there is no more need for a tensioner or matrix holder or retainer for initial positioning of wall molding means such as matrix bands.

Where the inflatable flexible container means are elongated, it becomes possible to partly surround the tooth being restored in order to place the inflatable flexible container means into the interdental space on either side of the tooth for holding the wall molding means on both sides of said tooth to restore decay of said both sides. In such a condition, the inflatable flexible container means, in addition to forcing the teeth apart from one another, elongate the tooth being restored in a direction opposite to the tooth holding apparatus. Such an elongation solicits the elastic memory of the tooth holding apparatus which will retract the tooth in its original position upon release of the force. Accordingly, there will be more room on either side of the tooth for the restorative procedure, and the teeth will recover a close contact preventing food impaction. Such an elongated inflatable flexible container means may have one end closed and another end open for connection to a fluid supply source for ease of manufacture and ease of use without interference of the fluid supply source in the buccal environment of the restoration site.

The inflatable flexible container means may have a first portion with a first outer diameter and at least a second portion with a second outer diameter, said first and second outer diameters different from one another, which configuration will allow easy matching of various dental configurations.

Where the inflatable flexible container means form an enclosure wherein a side wall thereof has an opening for connection to a fluid supply source, the device fully surrounds the tooth thereby becoming also applicable to restoration of a tooth without relying on interdental spacing and adjacent tooth to house and support the inflatable flexible container means.

Preferably, the inflation flexible container means have a substantially circular cross-section for ease of manufacture, and simplest adaptability to local conditions as, upon inflation that basic circular cross-section easily deforms in accordance with the contour of the room available around the tooth being restored.

The inflatable flexible container means may comprise means for supplying luminous energy to be effective for light curing of composite resin restorative materials. Within this frame, the inflatable flexible container means may comprise two lumina extending longitudinally therethrough wherein the luminous energy supplying means are arranged in one of said lumina the other lumen being connected to a fluid supply source, whereby there is no interference between the luminous energy arrangement and pressure setting equipment for the inflatable flexible container means. Also a one-lumen system is feasible since non-toxic natural enzyme derived, in situ activateable bio, respectively chemiluminescence, fluid can be used not only as light producing and transmitting means but also as pressure transmitting medium.

When the wall molding means are independent from the inflatable flexible container means, standard matrix material such as matrix bands may be used.

When the inflatable flexible container means are integral with the wall molding means, insertion of the whole in one step into the interdental space as well as removal therefrom also in one step greatly simplify matters for the practitioner. Respective positioning between inflatable flexible container means and wall molding means is systematic. In that case as well, the wall molding means may be formed of a matrix band.

When the wall molding means are formed by a wall of the inflatable flexible container means, simplification in handling and manufacturing goes even further, and a further step is achieved towards universality.

In sum, the invention relates to a dental medicine device for pressing a wall molding means against a decayed tooth wall for restoration thereof. The device includes expandable means for urging the wall molding means against the decayed tooth wall to hold restorative material inserted into the tooth. The expandable means include inflatable flexible container means for urging the wall molding means against the decayed tooth wall. The inflatable flexible container means may be elongated. The elongated inflatable flexible container means may have one end closed and another end open for connection to a fluid supply source. The inflatable flexible container means may have a first portion with a first outer diameter and at least a second portion with a second outer diameter, the first and second outer diameters different from one another. The inflatable flexible container means may form an enclosure, and a side wall thereof may have an opening for connection to a fluid supply source. The inflatable flexible container means may have a substantially circular cross-section. The inflatable flexible container means may include means for supplying luminous energy. The inflatable flexible container means may include two lumina extending longitudinally therethrough, and the luminous energy supplying means are arranged in one of the lumina, the other lumen being connected to a fluid supply source. The wall molding means may be independent from the inflatable flexible container means. The inflatable flexible container means may be integral with the wall molding means. The wall molding means may include a matrix band. The wall molding means may be formed by a wall of the inflatable flexible container means. The inflatable flexible container means may be made of a polyamid.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

DETAILED DESCRIPTION OF THE INVENTION

Figure 1:
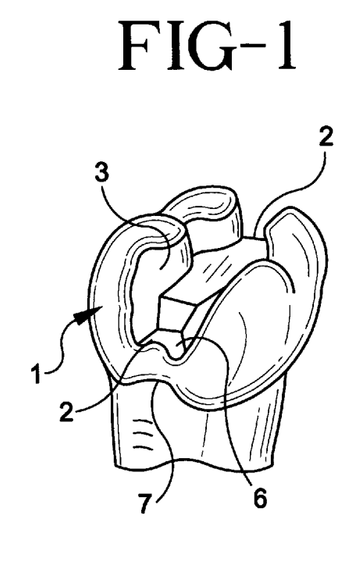
FIGS. 1–3 are perspective views illustrating a tooth prepared for restoration, prior art matrix band/wedge installation, and resulting restoration.

The tooth 1 shown in FIG. 1 has decay 2 on opposite sides thereof and presents a conventionally stepped cavity preparation 3 for restoration purposes.

Figure 2:
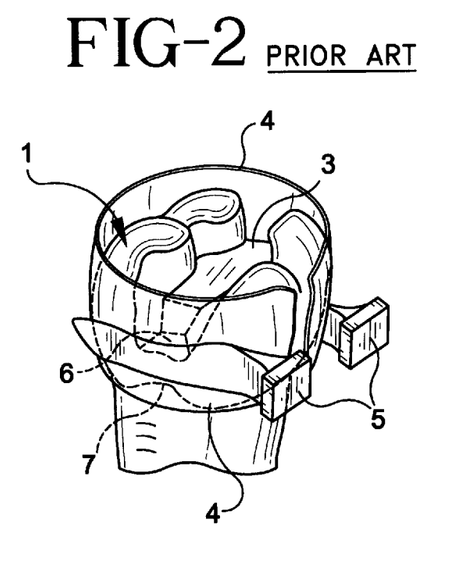
Figure 3:
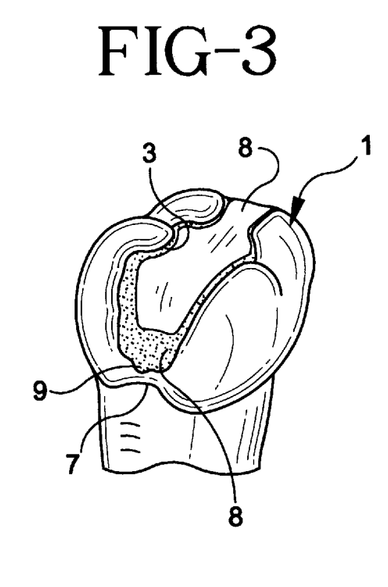

As shown in FIG. 2, restoration is being made with a matrix band 4 and two prior art wedges 5 have been forced between the tooth being restored and adjacent teeth (not shown) to cause the matrix band to be pressed against the tooth 1 at the floor 6 of the approximal cavity preparation 3. In the example shown, the cavity preparation 3 ends on a concave portion 7 of the tooth 1, and as a result, the wedges 5 cannot provide more than a tangential contact between the matrix band 4 and the tooth 1. As shown in FIG. 3, as the matrix band 4 cannot apply against the concave portion 7 of the tooth, the restorative material 8 inserted into the cavity preparation 3 causes an overhang 9 of surplus restorative material 8.

Figure 4:
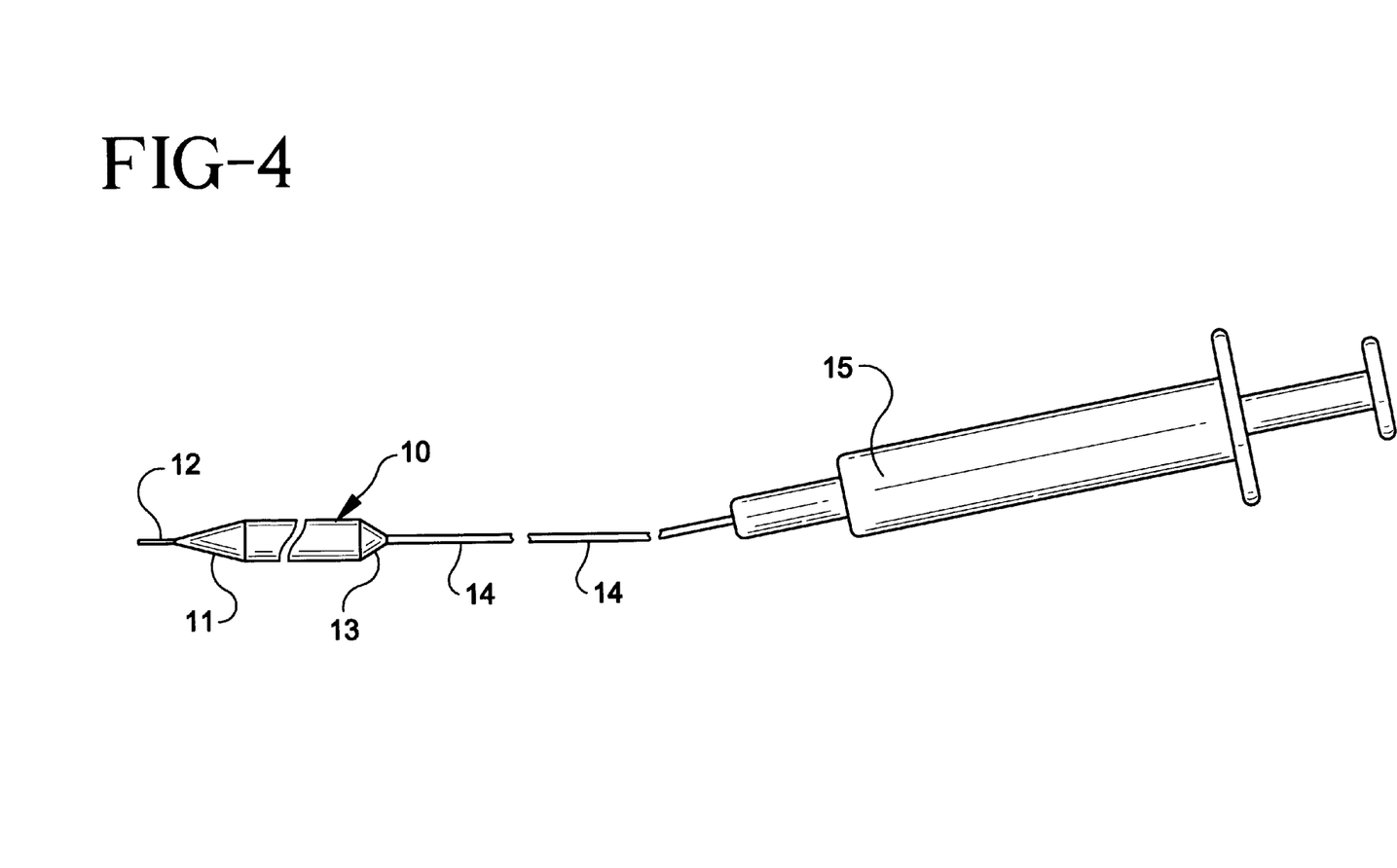
FIG. 4 is a side view of a first embodiment of the invention.

The first embodiment of the invention shown in FIG. 4, comprises inflatable flexible container means formed by an elongated balloon 10 the end 11 of which tapers to terminate in a closure tip 12. The other end 13 is open and connected to a duct 14 connected to an inflation fluid supply source, in this example a syringe 15. Preferably, the balloon 10 is made of a polyamid such as nylon, and it has a circular cross-section. Other materials, e.g., PET, and/or other cross-sectional geometries, e.g., triangular, are possible.

Figure 5:
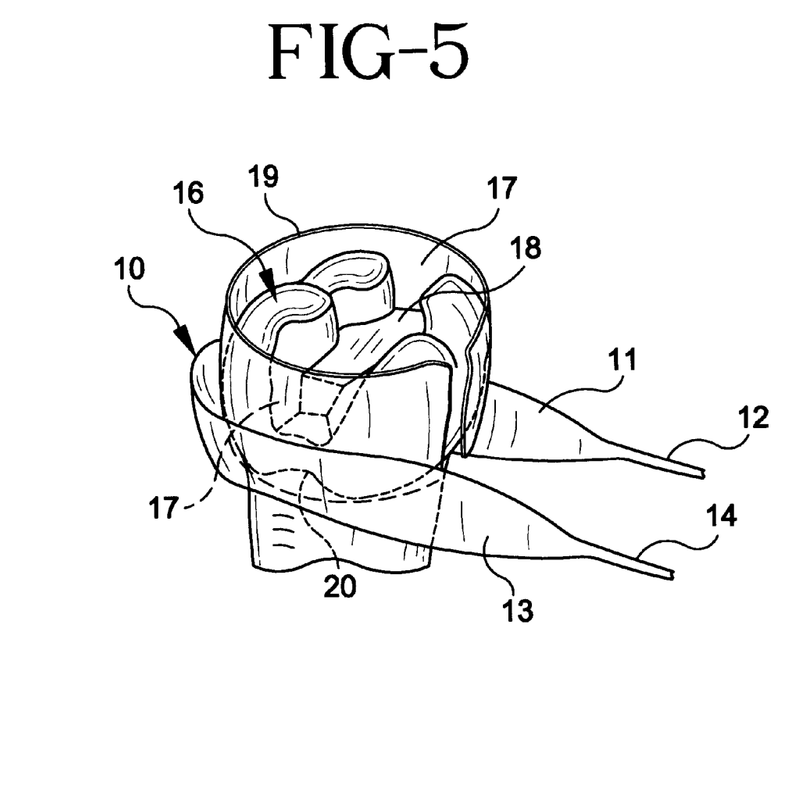
FIGS. 5 and 6 are perspective views of a tooth prepared for restoration with the first embodiment of FIG. 4 and resulting restoration.
Figure 6:
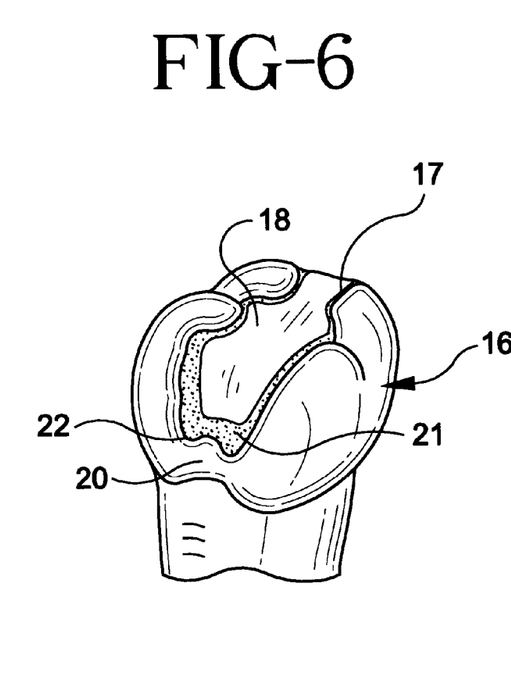

As shown in FIG. 5, a tooth 16 having decay 17 on opposite sides thereof presents a conventionally stepped cavity preparation 18 for restoration purposes. Mesial-occlusal-distal (MOD) restoration is made with a conventional matrix band 19 and the balloon 10 of FIG. 4 has been applied in part surrounding relationship to the tooth 16, between the tooth 16 and the adjacent teeth (not shown), so as to apply the matrix band 19 against the tooth 16 upon inflation thereof. In the example of FIG. 5, the cavity preparation 18 ends in a concave portion 20 of the tooth 16. Upon inflation, the balloon 10 evenly applies the matrix band 19 against the tooth 16, closely following the concave portion 20. FIG. 6 shows that, under such conditions, the restorative material inserted into the cavity preparation 18 properly seats at the margin floor 22 of the cavity preparation, without any overhang of surplus restorative material 21.

Figure 7:
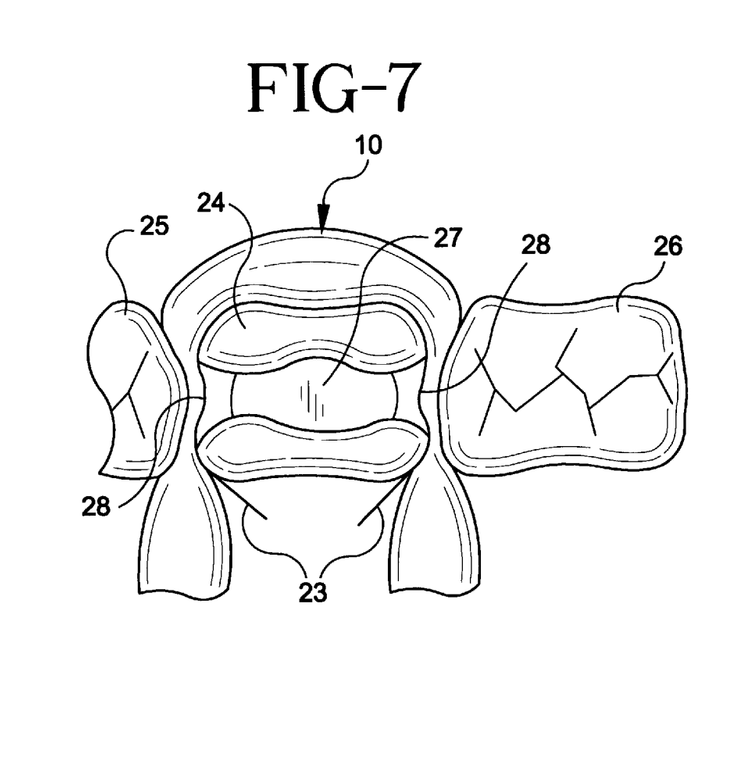
FIGS. 7 and 8 are top plan views of teeth prepared for restoration with the embodiment of FIG. 1.
Figure 8:
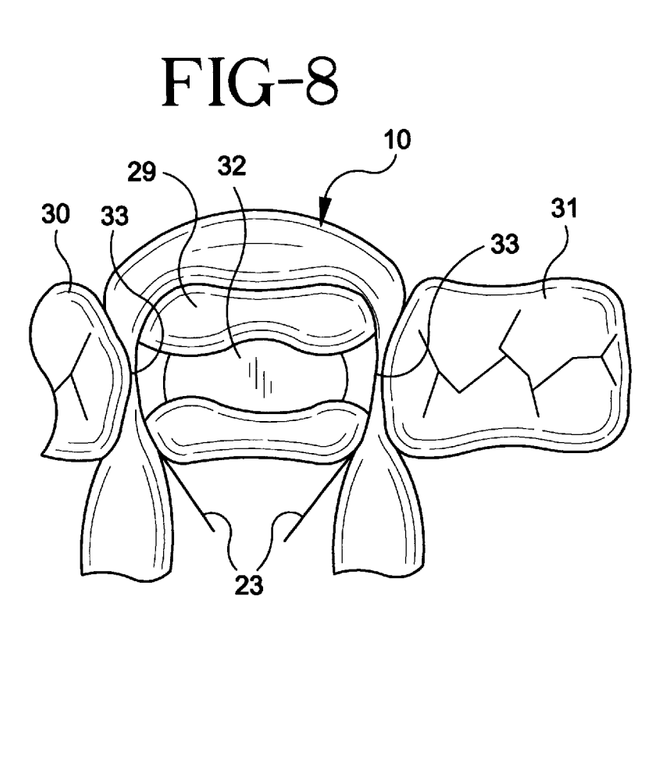

FIG. 7 shows the balloon 10 of FIG. 4 as applied around a matrix band 23 in part surrounding relationship to a tooth 24, between the tooth 24 and adjacent teeth 25 and 26. Tooth 24 has decay facing adjacent teeth 25 and 26 and MOD-cavity preparation 27 ends in concave portions 28 of the tooth 24. FIG. 8 shows the same configuration as FIG. 7 except that the decayed tooth 29 has decay facing adjacent teeth 30 and 31 and MOD-cavity preparation 32 ends in convex portions 33 of the tooth 29. In both the cases of FIGS. 7 and 8, the inflated balloon 10 properly and evenly applies the matrix band 23 against the central tooth 24 and 29.

Figure 9:
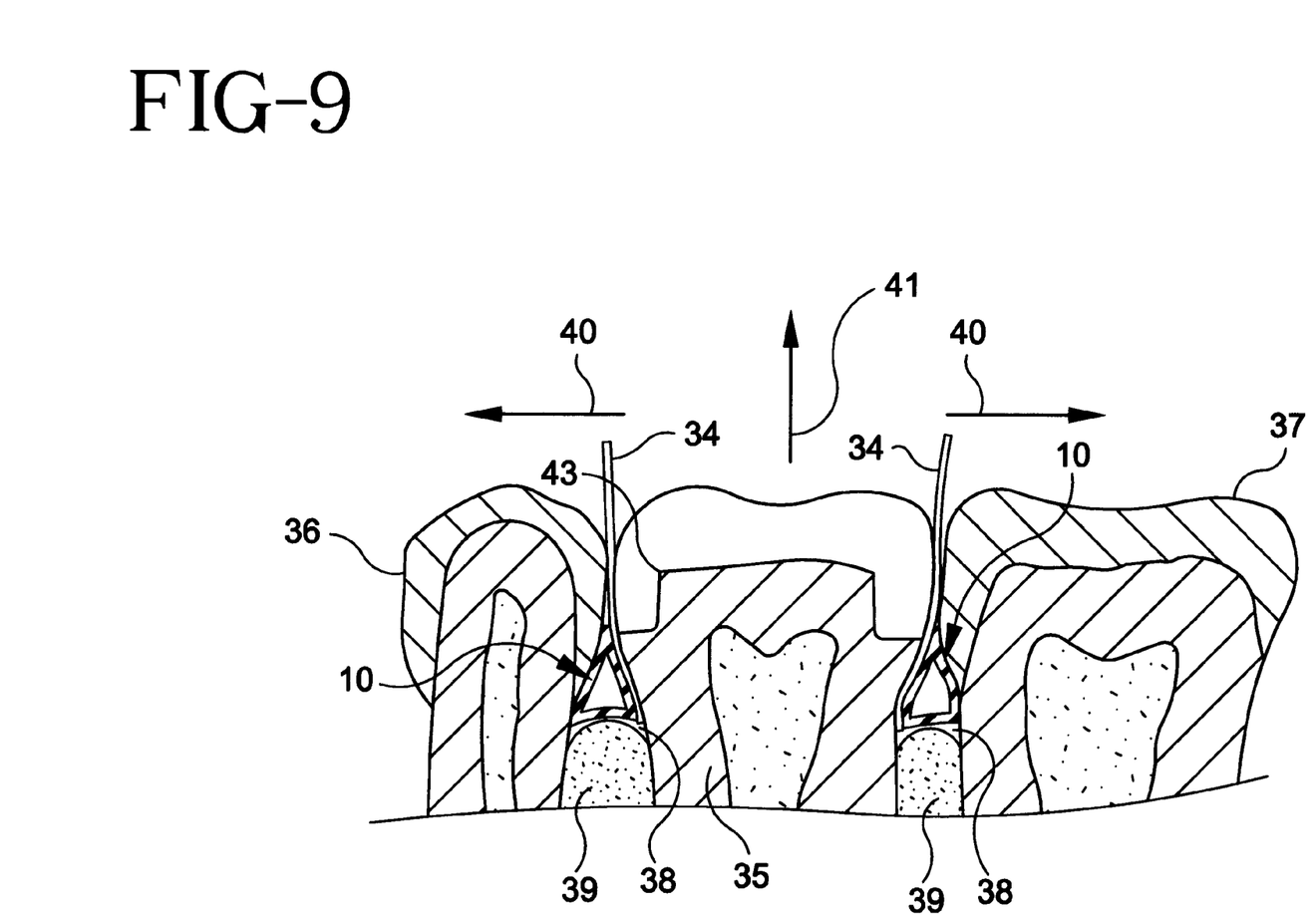
FIGS. 9 and 10 are elevational views illustrating the mode of operation of the embodiment of FIG. 4.
Figure 10:
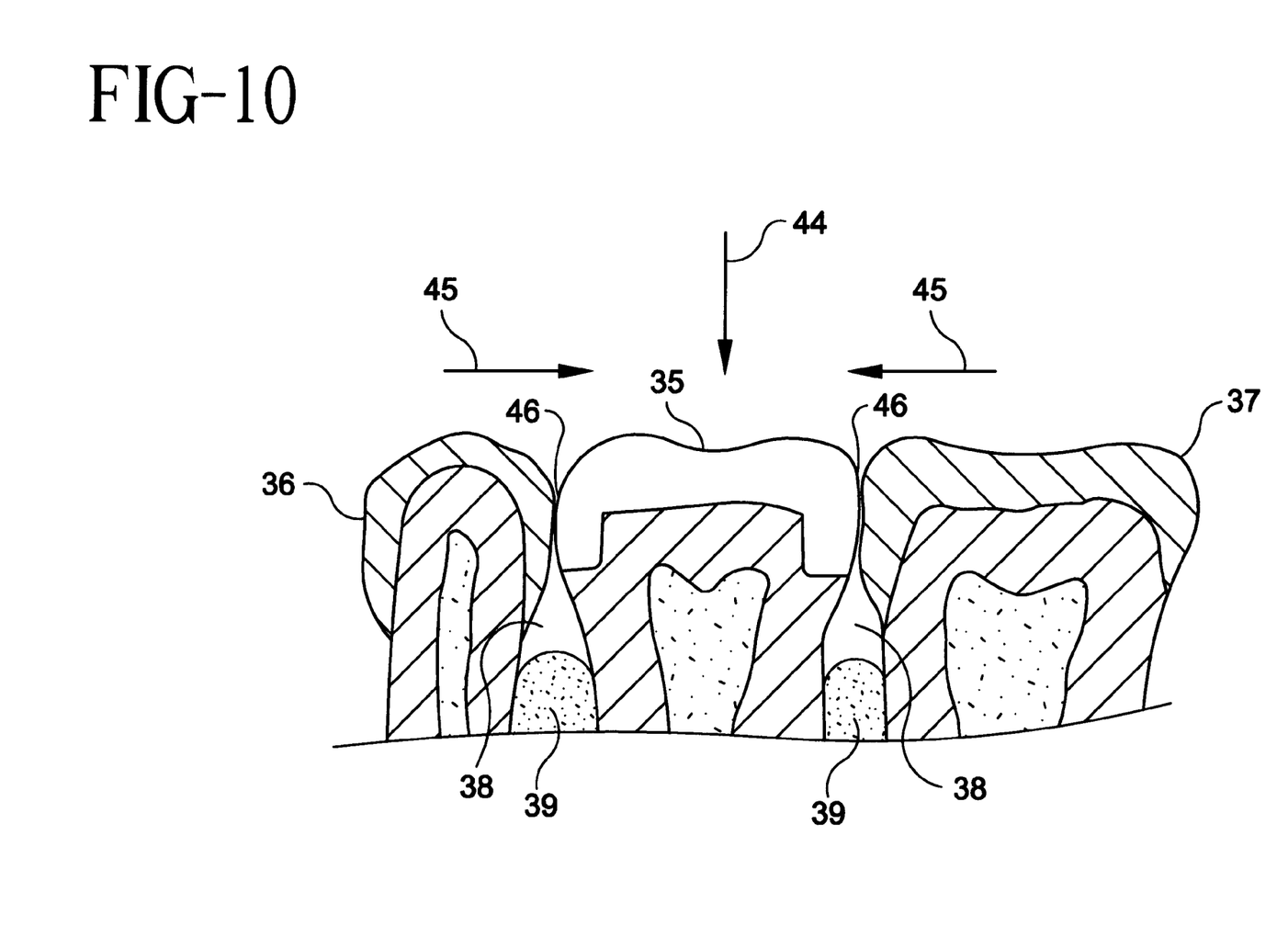

FIGS. 9 and 10 illustrate further details of the mode of operation of the embodiment of FIG. 4.

As shown in FIG. 9 balloon 10 is arranged against a matrix band 34 in part surrounding relationship to a tooth 35, between tooth 35 and adjacent teeth 36 and 37. Upon inflation, initially circular cross-section of balloon 10 deforms substantially triangularly in accordance with the contour of interdental space 38 between tooth 35 and adjacent teeth 36 and 37. Accordingly, inflated balloon 10 bears against the interdental papilla and tooth holding apparatus 39 simultaneously to bearing against tooth 35 and adjacent teeth 36 and 37. As a result of force repartition, balloon 10 urges the teeth 36 and 37 apart from tooth 35 as shown by arrows 40. Simultaneously, balloon 10 urges or elongates tooth 35 in a direction opposite to tooth holding apparatus 39 as shown by arrow 41. Matrix band 34 is closely applied to the MOD-cavity preparation 43 and cannot slip out of interdental space 38. As shown in FIG. 10, after the filling procedure of tooth 35, balloon 10 is deflated and withdrawn from interdental space 38. Matrix band 34 is also withdrawn from interdental space 38. As teeth 35, 36 and 37 are no more subjected to pressure of balloon 10, the elastic memory of tooth holding apparatus 39 periodontal ligaments will retract teeth 35, 36 and 37 in their original position as shown by arrow 44 and arrows 45, respectively. A tight contact 46 is thus assured between teeth 35, 36 and 37, preventing food impaction between the teeth at that level.

Figure 11:
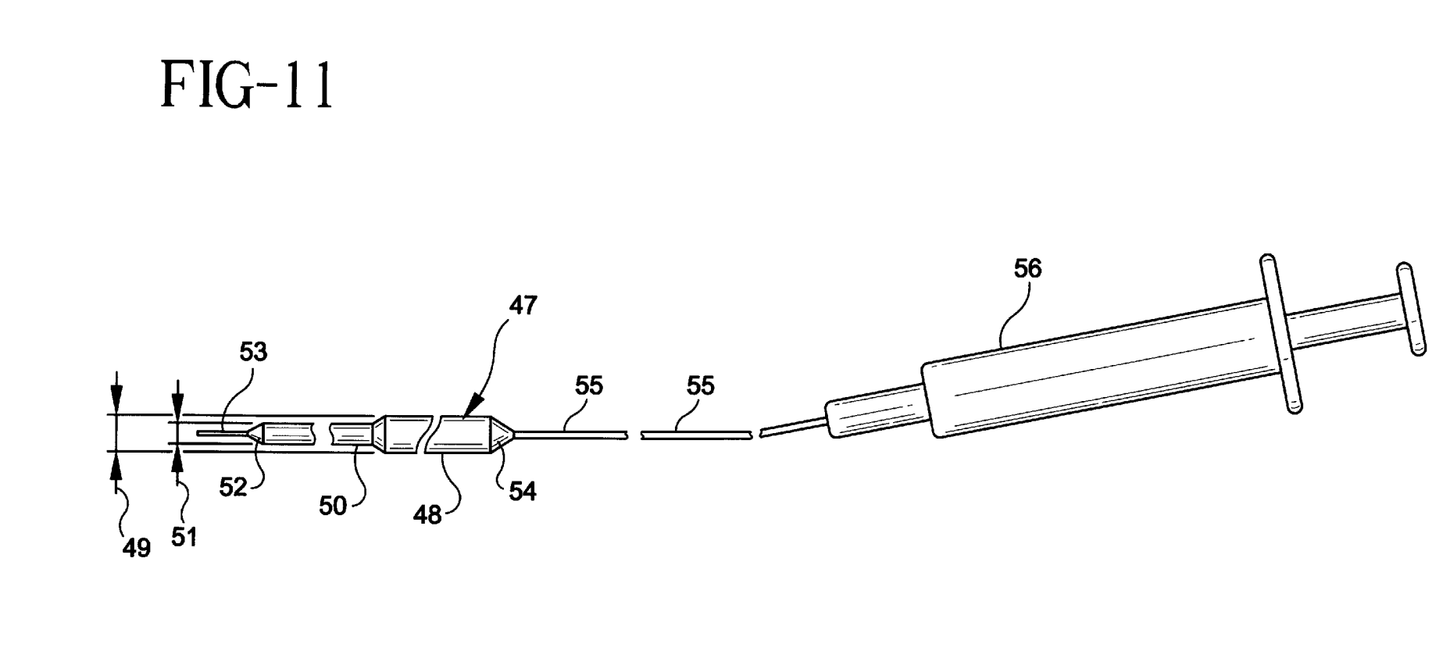
FIG. 11 is a side view of a second embodiment of the invention.

The second embodiment of the invention shown in FIG. 11 comprises inflatable flexible container means formed by an elongated balloon 47 with circular cross-section and having a first portion 48 with a first outer diameter 49 and a second portion 50 having a second diameter 51 smaller than first outer diameter 49. Second portion 50 tapers at its end 52 to terminate in a closure tip 53. The free end 54 of first portion 48 is open and connected to a duct 55 connected to inflation supply means formed by a syringe 56. Preferably balloon 47 is also formed of a polyamid.

Figure 12:
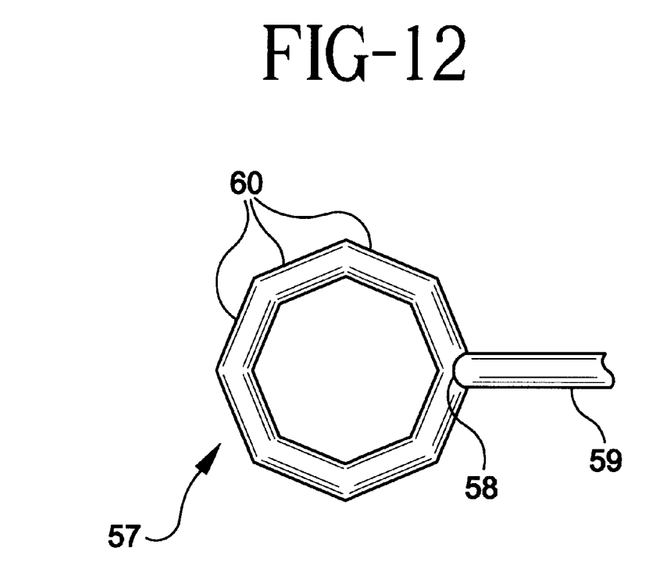
FIG. 12 is a top plan view of a third embodiment of the invention.

The third embodiment of the invention shown in FIG. 12 comprises inflatable flexible container means forming an enclosure 57 a side wall of which has an opening 58 for connection with a fluid supply source (not shown) via a duct 59. Enclosure 57 is formed of a plurality of tubular polyamid segments 60 welded to one another in a polygonal suite and communicating with one another and with duct 59.

Figure 13:
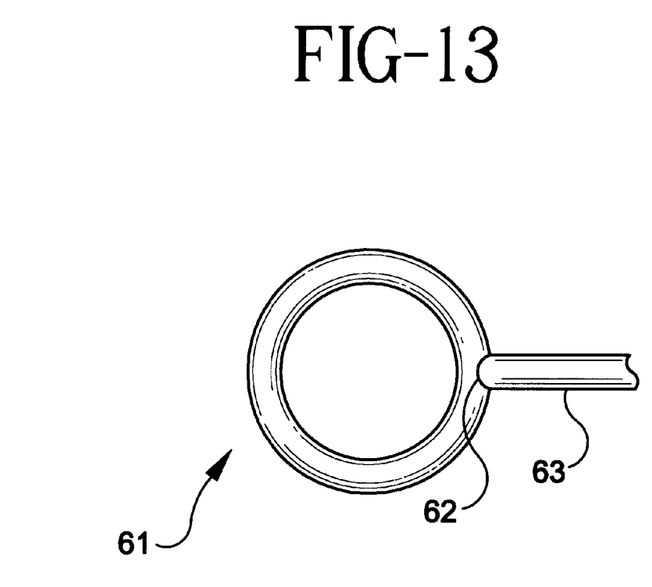
FIG. 13 is a top plan view of a fourth embodiment of the invention.

The fourth embodiment of FIG. 13 also comprises inflatable flexible container means forming an enclosure 61 a side wall portion of which has an opening 62 for connection to a fluid supply source (not shown) via a duct 63. Enclosure 61 is substantially toric, being formed of polyamid by known molding techniques. Cross-section of enclosure 61 is circular.

Figure 14:
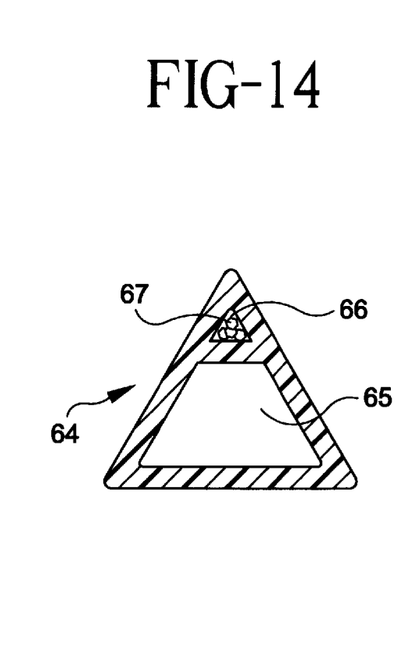
FIG. 14 is a cross-sectional elevation of a fifth embodiment of the invention.

The fifth embodiment of FIG. 14 comprises inflatable flexible container means formed by a polyamid balloon 64 having a substantially triangular cross-section. Balloon 64 has two lumina 65 and 66, lumen 65 being for connection to a fluid supply means (not shown), and lumen 66 containing luminous energy supplying means such as, for example, a fluid which can be activated by means of bio, respectively chemiluminescence, to produce curing light to polymerize the bonding agent and the first incremental composite resin insertion at the margin of the proximal cavity floor, the fluid containing light reflecting flakes 67 distributed therein.

Figure 15:
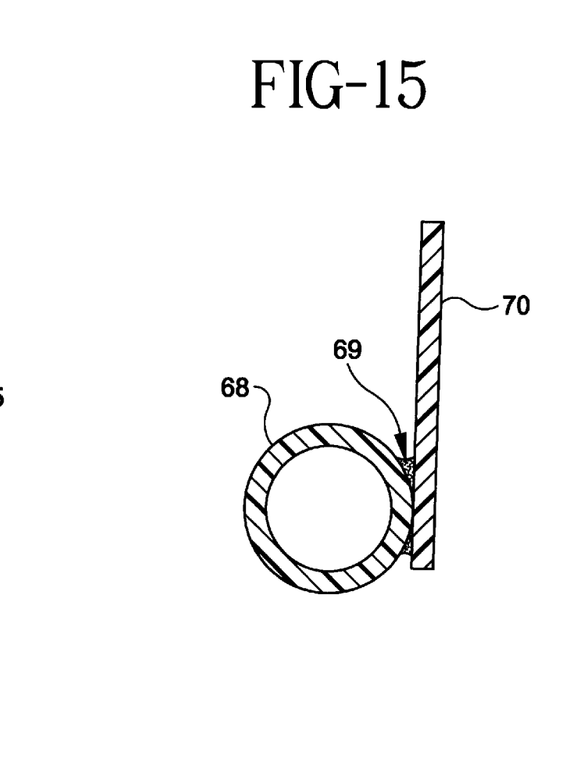
FIG. 15 is a cross-sectional elevation of a sixth embodiment of the invention.

In the embodiment of FIG. 15, an elongated polyamid balloon 68 is longitudinally affixed, for example adhesively or by welding as at 69, to a matrix band 70, being thus integral therewith.

Figure 16:
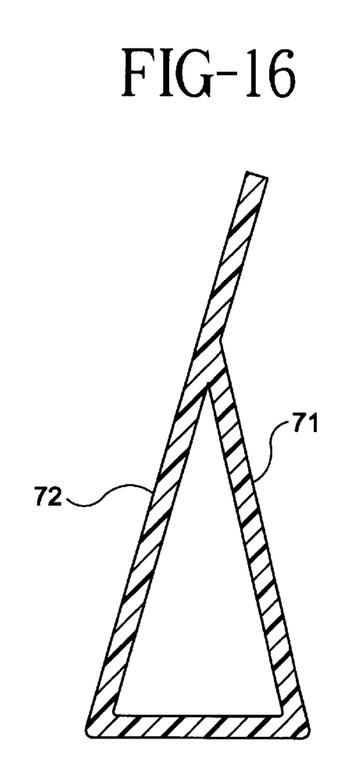
FIG. 16 is a cross-sectional elevation of a seventh embodiment of the invention.

In the embodiment of FIG. 16, an elongated polyamid balloon 71 has a substantially triangular cross-section. One wall 72 of such a balloon, which extends beyond the triangular section, forms a matrix band configuration or wall molding means which will be pressed against the tooth upon inflation of the balloon 71.

Variants are available without departing from the scope of the invention. For example, a short pad-like balloon may be used instead of the elongated balloon configuration shown, for situations where the device is for use in restoration of only one side decay of a tooth, i.e., so-called mesial-occlusal (MO) or occlusal-distal (OD) cavity situations.

Cross-sections of the inflatable flexible container means described as circular may be other than circular, and similarly cross-section described as triangular may be circular or otherwise.

In the embodiment of FIG. 11, there may be more than two portions of different diameter.

In the embodiment of FIG. 14, the balloon may have only one lumen for the fluid supply and the luminous energy supply means. Same the luminous energy supplying means may be other than light reflecting flakes, for example, chemical components.

And of course other materials than polyamid may be used to form the inflatable flexible container means.

It will be evident from considerations of the foregoing that the Interdental Balloon may be constructed using a number of methods, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A dental device for pressing a wall molding means against a decayed tooth wall for restoration thereof, comprising:

expandable means for urging the wall molding means against the decayed tooth wall to hold restorative material inserted into the tooth, wherein the expandable means comprises inflatable flexible container means for urging the wall molding means against the decayed tooth wall, and the inflatable flexible container means comprises two lumina extending longitudinally therethrough, and wherein a luminous energy supplying means is arranged in one of the lumina, the other of the lumina being connected to a fluid supply source.

2. The device according to claim 1 wherein the inflatable flexible container means is elongated.

3. The device according to claim 2 wherein the elongated inflatable flexible container means has one end closed and another end open for connection to a fluid supply source.

4. The device according to claim 1 wherein the inflatable flexible container means has a first portion with a first outer diameter and at least a second portion with a second outer diameter, the first and second outer diameters different from one another.

5. The device according to claim 1 wherein the inflatable flexible container means forms an enclosure, and wherein a side wall thereof has an opening for connection to a fluid supply source.

6. The device according to claim 1 wherein the inflatable flexible container means has a substantially circular cross-section.

7. The device according to claim 1 wherein the wall molding means is independent from the inflatable flexible container means.

8. The device according to claim 1 wherein the inflatable flexible container means is integral with the wall molding means.

9. The device according to claim 7 wherein the wall molding means comprises a matrix band.

10. The device according to claim 1 wherein the wall molding means is formed by a wall of the inflatable flexible container means.

11. The device according to claim 1 wherein the inflatable flexible container means is made of a polyamide.

* * * * *